US00PP24573P3

(12) United States Plant Patent
Egger

(10) Patent No.: US PP24,573 P3
(45) Date of Patent: Jun. 24, 2014

(54) ***HEUCHERA* PLANT NAMED 'SWEET TART'**

(50) Latin Name: ***Heuchera* hybrid**
Varietal Denomination: Sweet Tart

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 141 days.

(21) Appl. No.: 13/507,973

(22) Filed: Aug. 10, 2012

(65) Prior Publication Data

US 2014/0047607 P1 Feb. 13, 2014

(51) Int. Cl.
*A01H 5/00* (2006.01)

(52) U.S. Cl.
USPC ..... Plt./440

(58) Field of Classification Search
CPC ..... A01H 5/00; A01H 5/02; A01H 5/12
USPC ..... Plt./440
See application file for complete search history.

*Primary Examiner* — Susan McCormick Ewoldt
(74) *Attorney, Agent, or Firm* — Klarquist Sparkman, LLP

(57) ABSTRACT

A new and distinct *Heuchera* plant characterized by small yellow spring leaves that mature to lime green, winter leaves of olive green with red veins, bright pink in wands, very free flowering on short, dark flower stalks, a small, multi-crowned, low mounding habit, and excellent vigor.

1 Drawing Sheet

Botanical denomination: *Heuchera* hybrid.
Variety designation: 'Sweet Tart'.

BACKGROUND OF THE INVENTION

The present invention relates to a new and distinct cultivar of *Heuchera* and given the cultivar name of 'Sweet Tart'. *Heuchera* is in the family Saxifragaceae. *Heuchera* 'Sweet Tart' originated from a controlled cross between *Heuchera* K273-1, a proprietary non-commercial hybrid, as the seed parent, and *Heuchera* K412-1, a proprietary non-commercial hybrid, as, as the pollen parent.

Compared to the seed parent, *Heuchera* K273-1, the new cultivar has lime rather than green leaves and a smaller habit.

Compared to the pollen parent, *Heuchera* K412-1, the new cultivar has a smaller habit and pink rather than red flowers.

Compared to *Heuchera* 'Havana', U.S. Plant Pat. No. 22,087, the new cultivar has more crowns, smaller leaves that are less lobed, bright pink rather than rose colored flowers, and is more free-flowering.

This new *Heuchera* is uniquely distinguished by:

1. small yellow spring leaves that mature to lime green,
2. bright pink flowers in wands,
3. very free-flowering and repeat blooming on short, dark flower stalks,
4. small, multi-crowned, low mounding habit, and
5. excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

FIG. 1 shows a one-year-old plant of *Heuchera* 'Sweet Tart' growing in a one gallon pot in a cool greenhouse in July in Canby, Oreg.

DETAILED PLANT DESCRIPTION

The following is a detailed description of the new *Heuchera* cultivar based on observations of two-year-old specimens growing in one gallon containers in a cold greenhouse in March in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The *Royal Horticultural Society Colour Chart,* 2007 edition.

Plant:

*Form.*—Basal rosette, herbaceous perennial.
*Hardiness.*—USDA Zone 4 to 9.
*Size.*—13 cm tall from top of the foliage to the soil and 24 cm wide.
*Habit.*—Mounding.
*Vigor.*—Excellent.

Leaf:

*Type.*—Simple.
*Arrangement.*—Rosette.
*Shape.*—Broadly ovate to orbicular.
*Lobing/division.*—5 to 7 lobes with shallow secondary lobes.
*Venation.*—Palmate.
*Number.*—About 40.
*Margins.*—Crenate.
*Apex.*—Mucronulate.
*Base.*—Cordate.
*Blade size.*—Grows to 7 cm long and 6.5 cm wide.
*Texture.*—Supple.
*Surface texture.*—Short glandular on top and bottom side.

*Petiole description.*—Grows to 10 cm long and 1.5 mm wide, short glandular hairs, Yellow Green145A.

*Leaf color.*—Topside, new leaves in spring Yellow Green N144A darkening to 144A in summer with veins 145C, winter leaves are closest to 146B with a very slight white veil and slightly darkened veins (tinted Greyed Orange 177D).

Inflorescence:

*Size.*—Grows to 4 cm wide and 9 cm long.

*Type.*—Thyrse.

*Number of flowers per thyrse.*—About 100.

*Number of thyrse.*—About 25 in the first spring flush, reblooming all summer to frost.

*Peduncle.*—Grows to 11 cm long, 3 mm wide at base, Greyed Orange 178A, glandular hairs.

*Pedicel.*—Variable in size, with glandular hairs, Greyed Orange 178A.

*Bloom period.*—May through October in Canby, Oreg.

Flower bud:

*Size.*—3 mm wide and 5.5 mm long.

*Description.*—Glandular puberulent, ovoid, down facing.

*Color.*—Red Purple 64A.

Flower:

*Type.*—Perfect.

*Shape.*—Campanulate.

*Size.*—6 mm long and 7 mm wide.

*Corolla description.*—5 petals, 2 mm long and 0.5 mm wide, narrowly spatulate, margins entire, tip acute, glabrous top and bottom, Red Purple 65D.

*Calyx description.*—Campanulate, 6 mm long and 7 mm wide, with 5 lobes divided ½ way to the base, each 2 mm wide and 3 mm long, glandular hairs outside and inside, tips obtuse, margin entire; color outside Red Purple 64D with lobe tips 64A, inside Red Purple 65B with lobe tips 64A.

*Stamen description.*—5 in number, filaments 2.3 mm long, White N155B, anthers 0.2 mm, Orange 27A, pollen none.

*Pistil description.*—1, 2-beaked, 4 mm long and 2 mm wide; ovary 1.5 mm long and 2 mm wide Yellow Green 4C,; style 2.5 mm long, Yellow 4D.

*Fragrance.*—None.

*Lastingness.*—Each thyrse blooms for about 3 weeks on the plant.

Fruit:

*Type.*—Two-beaked ovoid capsule.

*Fertility.*—Low.

*Color.*—Greyed Brown 199C.

*Size.*—4 mm long and 3 mm wide.

Seed:

*Shape.*—Linear.

*Size.*—2 mm long.

*Color.*—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

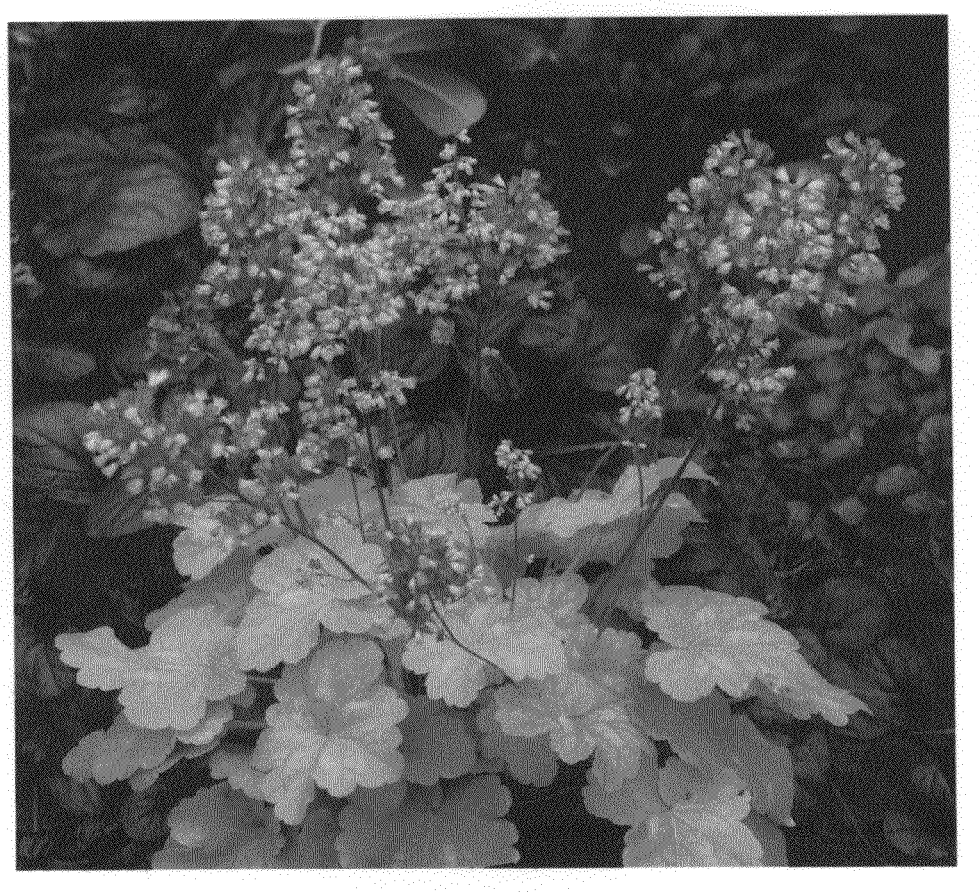

* * * * *